(12) United States Patent
Yakopson et al.

(10) Patent No.: US 6,578,433 B1
(45) Date of Patent: Jun. 17, 2003

(54) METHOD AND DEVICE FOR MEASURING DONNING PROPERTIES OF HOSIERY

(75) Inventors: Simon Myron Yakopson, Hickory, NC (US); John David Loveless, Hickory, NC (US); Kevin Michael Tucker, Matthews, NC (US)

(73) Assignee: Beiersdorf-Jobst, Inc., Charlotte, NC (US)

(*) Notice: Subject to any disclaimer, the term of this patent is extended or adjusted under 35 U.S.C. 154(b) by 0 days.

(21) Appl. No.: 09/787,598
(22) PCT Filed: Sep. 17, 1999
(86) PCT No.: PCT/US99/21676
§ 371 (c)(1),
(2), (4) Date: Mar. 20, 2001
(87) PCT Pub. No.: WO00/18344
PCT Pub. Date: Apr. 6, 2000

Related U.S. Application Data
(60) Provisional application No. 60/101,700, filed on Sep. 25, 1998.

(51) Int. Cl.[7] ................................................. G01N 3/08
(52) U.S. Cl. ............................................ 73/832; 73/824
(58) Field of Search ........................ 73/826, 827, 818, 73/865.6, 832, 824; 223/61, 112; 376/230; 607/122; 606/232

(56) References Cited

U.S. PATENT DOCUMENTS

| | | | | |
|---|---|---|---|---|
| 4,358,961 A | * | 11/1982 | Woods, Jr. | 73/827 |
| 5,100,610 A | * | 3/1992 | Pirl et al. | 376/260 |
| 5,450,990 A | * | 9/1995 | Migliorini | 223/61 |
| 5,651,483 A | * | 7/1997 | Bell et al. | 223/112 |
| 5,967,495 A | * | 10/1999 | Kaminski et al. | 254/134.4 |
| 6,041,660 A | * | 3/2000 | Fujitaka et al. | 73/826 |

* cited by examiner

Primary Examiner—Max Noori
(74) Attorney, Agent, or Firm—Alston & Bird LLP

(57) ABSTRACT

There is provided a method for testing the forces experienced by a wearer when donning a tubular article. The method includes securing one end of a tubular hosiery article to be tested to a support, inserting a tension tester head within the tubular body and measuring the force against the article surface as the tester head passes through the article. An apparatus for performing this method is also disclosed. The tester head has a geometric shape that may be advanced by withdrawing the head through the hosiery or the hosiery may be drawn past the tension head.

11 Claims, 3 Drawing Sheets

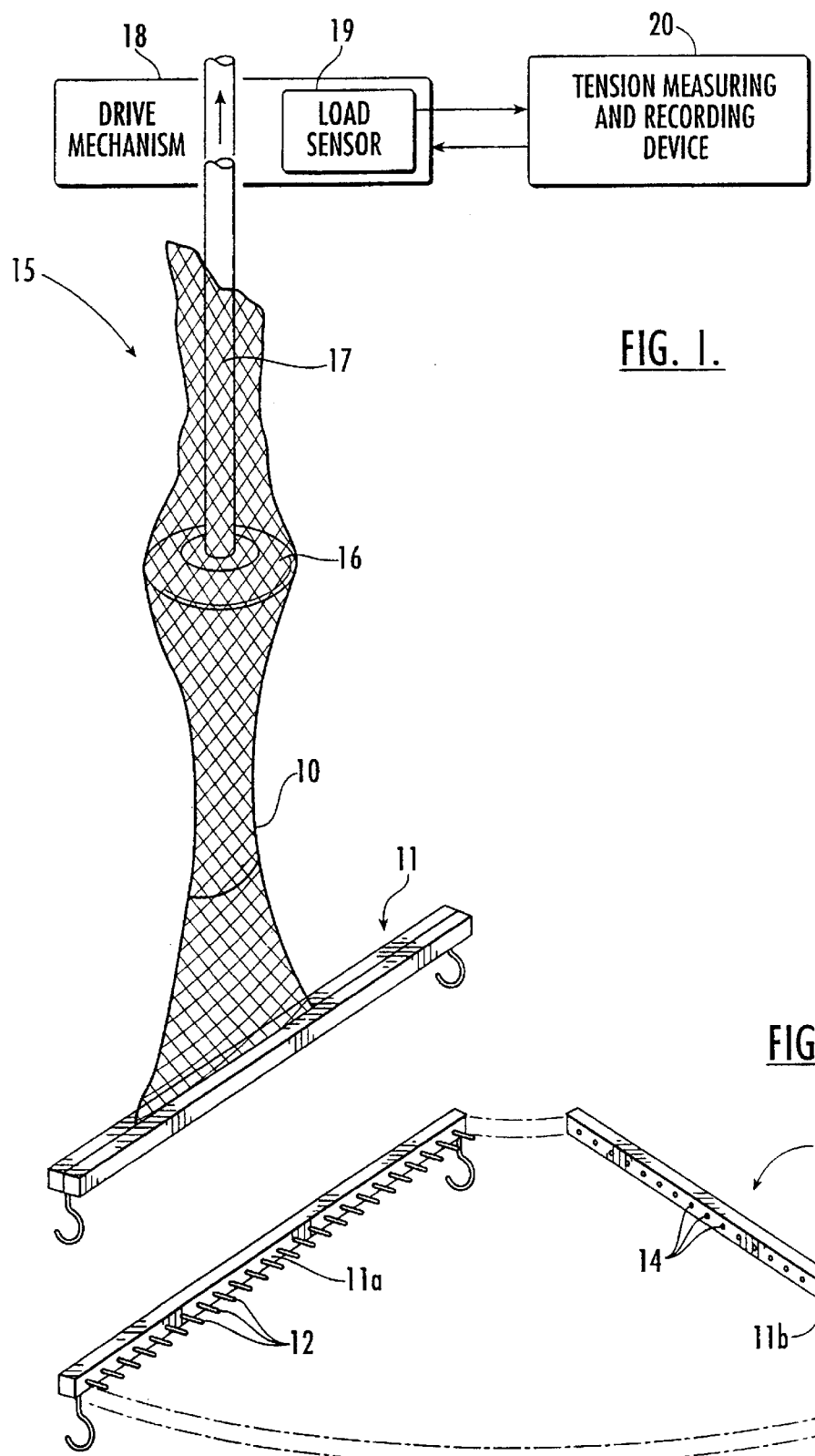

METHOD AND DEVICE FOR MEASURING DONNING PROPERTIES OF HOSIERY

CROSS-REFERENCE TO RELATED APPLICATIONS

This application claims priority from Provisional Application Ser. No. 60/101,700 entitled Method For Evaluation Of Donning Properties Of Hosiery And Device To Conduct It, filed Sep. 25, 1998.

FIELD OF THE INVENTION

The invention relates to a method for evaluating the donning properties of hosiery and a device which can be used to perform the method. More specifically, the invention relates to a method for simulating and measuring frictional and compressive forces that a patient would experience when donning a stocking, and an apparatus for measuring those forces.

BACKGROUND OF THE INVENTION

Compression stockings are commonly used for a wide variety of medical purposes including the prevention of the formation of embolisms in the legs of bed-ridden or sedentary people, to enhance circulation, and to assist in controlling swelling. Stockings for the legs are generally circularly knit and designed to provide a certain degree of compression to an underlying limb when worn. In many cases, the compression is graduated along the length of the stocking such that the stocking not only conforms to the contours of a wearer's leg, but the pressure in different sections of the stocking is varied according to where more or less compression is desired for the particular wearer. For example, one type of compression stocking divides the leg of a wearer into elements A through E where A corresponds to the foot, B corresponds to the ankle, C corresponds to the calf, D corresponds to the region below the knee and E corresponds to the knee, and selected ones of the regions A through E can be knit or otherwise constructed or treated to provide more or less compression in a specific corresponding region of the wearer's body.

To determine the amount of compression provided by a particular stocking, a variety of methods can be utilized. One popular method involves the provision of a three-dimensional substantially leg-shaped device having two bars which extend along the leg portion of the device. At least one of the two bars contains sensors along its length. A stocking is donned on the device in the manner it would be worn on a wearer's leg, and the bars are spread apart to a specific span designed to correspond to the girth of the human leg which the stocking is adapted to fit. The sensors on the thus-spread bars then register the compression being provided by the stocking along the specific regions thereof. Although this can provide a good reading of the compression provided by the stocking once it is donned, it is a static test and therefore does not give an indication of the other forces created during donning of the stocking by the wearer.

An alternative test involves clamping the stocking and stretching it, then allowing it to recover, while measuring the outgoing tension and forces resisting the return to the original dimension. However, this method does not take into account the effects on the fabric in the vertical direction as a result of the test (e.g., due to the fact that when a knit tubular fabric is stretched at discrete points in the coursewise direction, the tube narrows above and below the point where the fabric is being stretched outwardly.)

In order to obtain an indication of the forces experienced by the wearer's limb as the stocking is donned, stockings are often tested for the degree of friction which they exhibit when they slide along an object such as a wearer's limb, with the expectation that the lower the friction, the more easily the article can be donned by the wearer. Such friction tests generally involve placing a piece of the fabric on a flat surface, then putting a carriage on the fabric and measuring the force it takes to slide the carriage across the fabric. While such tests can give an absolute type of value for the surface friction, they are less appropriate for testing compression-type stockings and in particular, those with graduated degrees of compression. Furthermore, such tests fail to account for the changes the knit fabric undergoes during the donning process. While the fabric is stretched at various positions along its length, such as the longitudinal and transverse deformation and effects thereof on the fabric and article, the stretch resistance and recovery power of the elastic components forming part of the article causes friction between fibers and yarns in the fabric.

With the foregoing in mind, it is an object of the present invention to provide a hosiery testing device including a means to anchor the hosiery in place during the testing and a tester head connected to means for moving the tester head through the hosiery article or moving the hosiery article past the tester head and means for measuring the force used to advance the tester head through the hosiery article. It is a further object of the present invention to provide a method for measuring the donning properties of hosiery.

SUMMARY OF THE INVENTION

The apparatus of the present invention includes a support for securing one end of the hosiery in a permanent position, a tester head attached to a rod adapted to be pulled or pushed through the tubular article and means for moving the geometric body of the tension tester head through the tubular article, a load sensor for measuring the tension within the tubular article and a tension measuring and recording device.

It has been found that the donning properties of hosiery may be obtained by securing one end of a tubular article such as hosiery to be tested to a support, inserting a tension testing head within the tubular body, advancing the tester head through the tubular article, and measuring the force used to advance the tester head and the expansion of the tubular article. The tester head has a geometric shape that may be advanced by withdrawing the head through the hosiery or the hosiery may be drawn past the tension head.

BRIEF DESCRIPTION OF THE DRAWINGS

Other objects, features and advantages of the present invention will become apparent from the detailed description of the invention that follows, and from the accompanying drawings in which:

FIG. 1 illustrates an embodiment of the testing device of the present invention, FIG. 2 is an enlarged view of the pin assembly used in connection with the testing device of the present invention;

DETAILED DESCRIPTION OF THE INVENTION

Figure 3:
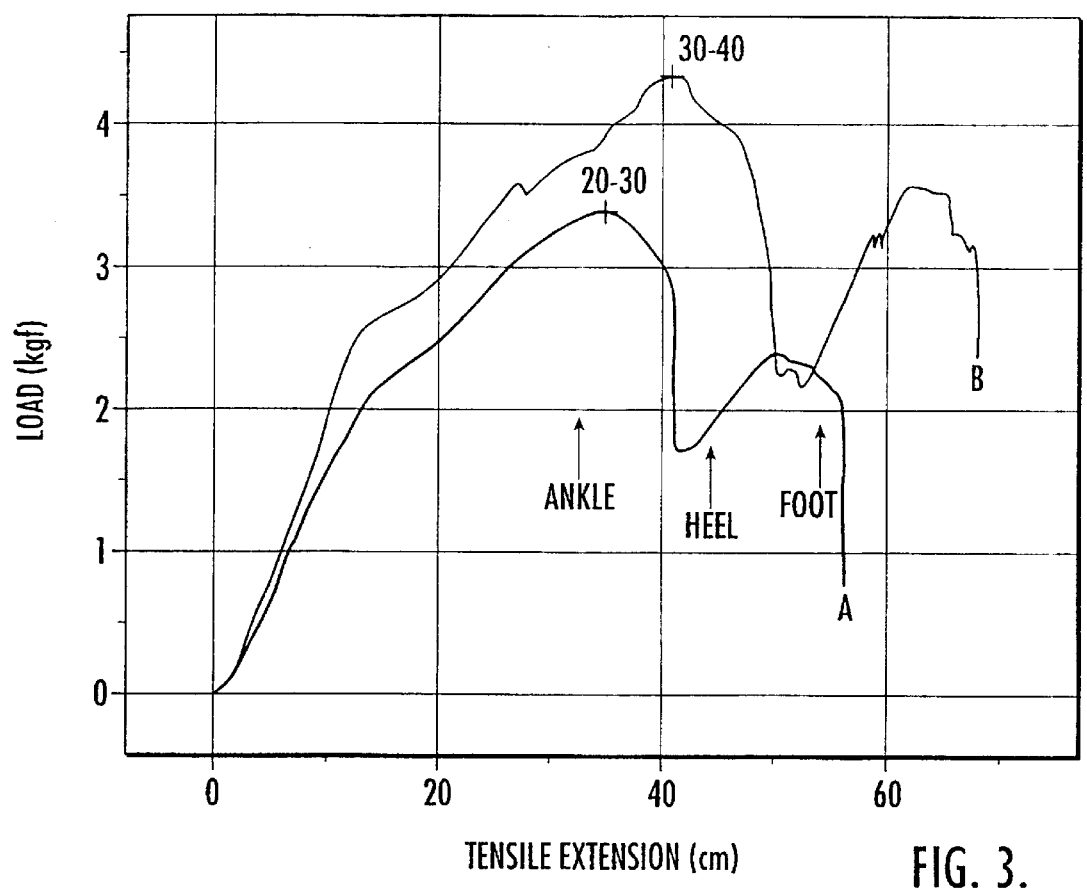
FIG. 3 illustrates the influence of the degree of compression from two different stockings manufactured by the same manufacturer on the forces during donning as the tester head passes through different portions of the stockings in accordance with a method of this invention.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Referring now to FIG. 1, the device of the present invention utilizes a tension testing head 15 in combination with a conventional device designed to test tension, to obtain a measurement of the forces involved when donning a stocking. In the embodiment shown in FIG. 1, one end of a stocking 10 to be tested is retained in the support 11. In this case, a pin bar assembly is utilized to retain one end of a stocking.

The apparatus of this invention further includes a tension tester head 15 having a geometric body 16 which is adapted for motion relative to the stocking support (e.g. pin bar 11). In the embodiment shown in FIG. 1, the tension testing head 15 is moved by way of a rod 17, which in turn is secured to a drive mechanism 18, having a load sensor 19 and a tension measuring and recording device 20. The invention is not intended to be limited to any specific type of measuring and recording device, rather any available equipment capable of measuring and recording tension can be used to perform the instant method. Machines which have been found to perform as in the invention are commonly sold under the INSTRON brand name.

The geometric body 16 is preferably shaped to simulate at least a portion of the foot as it extends through the stocking. For example, in FIG. 1, the geometric body is provided in the form of a torus or disc shape which is sized to approximate the thickest portion of the wearer's foot and leg, i.e., that portion extending from the talus around the heel. However, it is to be noted that other shapes are contemplated within the scope of the instant invention, such as foot-shaped, oval, football-shaped, or half football-shaped, or any other shape or configuration. In addition, although the torus-shaped geometric body has been illustrated as being positioned on the rod so that it extends outwardly substantially perpendicular to the rod, it is also contemplated that the body can be positioned at other angles or orientations as desired. Furthermore, the body can be of a single piece of material, or a plurality of pieces, and can be substantially rigid or somewhat flexible or even pivotable, depending on the test that is to be performed.

In a preferred form of the invention, the geometric body 16 is selected to have frictional characteristics similar to those of the item that the stocking would be donned on in use. For example, where the donnability of a stocking which is to be worn on an uncovered leg of a human is to be tested, it is desired that the geometric body be made from a material which would have frictional characteristics similar to those of a person's leg. It has been found that geometric bodies 16 made from nylon, such as nylon 6, work particularly well in this end use. Polyethylene bodies have also been found to work well. However, any other type of material could be used including but not limited to plastics, metal, smooth or textured surfaces, coated surfaces, hairless or hairy surfaces, leather, wood, or the like. Furthermore, while the term "geometric" has been used to describe the body, this term is not meant to limit the shape to those which are regular or have a defined name, rather it is intended to encompass all shapes and configurations of body which would perform in the instant invention (in other words, essentially any three-dimensional shape).

In addition, different sizes of geometric bodies can be provided based on the particular size of product to be tested. For example, because the widest circumference of an average person's foot is generally about 1.5 times the maximum ankle circumference, it can be desirable to provide geometric bodies having circumferences approximating about 1.5 times the circumference of the ankle for which the size of stocking to be tested is designed to fit. Similarly, where, for example, it is expected that swelling in the lower leg will have occurred, a different factor such as 1.1 times the ankle circumference can be used. In the embodiment of the invention used for the test results illustrated in the figures, the torus was about an inch thick as well (and formed from nylon 6), in order to provide sufficient rigidity and thickness to test even those stockings having a high resistance to being donned.

As illustrated in FIG. 2, the support may be a pin bar assembly 11 which utilizes a first bar 11a having a plurality of pins 12 extending outwardly therefrom while second bar 11b includes a mating set of orifices 14 which are adapted to receive the pins of bar 11a. In this way, one end of a stocking 10 can be placed across the bar 11a such that the pins extend therethrough, and the second bar 11b can be secured so that the pins are received within the orifices, thereby capturing the end of the stocking. Although this specific retention device is illustrated, it is noted that any type of device which is capable of holding or otherwise securing an end of the stocking could be used within the scope of the invention.

In the embodiment shown in FIG. 1, the stocking support, pin bar 11, is designed to be held stationary to hold the stocking in a stationary position while the geometric body 16 is adapted to move vertically away from the pin bar such that the body slides along the length of the tube-shaped stocking. Because the motion of the geometric body 16 is controlled by the tension tester, the load versus the tensile extension of the stocking can therefore be charted as shown for example in FIGS. 3 and 4. For example, FIG. 3 illustrates a donning test performed on stockings of two different compressions. The first being that having a 20–30 mm Hg compression while the second stocking has a 30–40 mm Hg compression. In the instant case, the toe opening of the stocking is opened in order that the rod and geometric body can extend therethrough. Therefore, the first declining slope on each of the two curves illustrates where the geometric body extends through the heel portion of the stocking, whereas the second declining and end portion represent where the geometric body is pulled out from the open toe of the stocking.

In performing a preferred method of the invention, a first end of the stocking is placed around the geometric body and then at least one of the stocking and/or the geometric body is moved relative to the other such that the geometric body slides along the interior of the stocking. In this way, the force required to move the geometric body and the stocking relative to each other can be recorded by the tension tester. In the embodiment illustrated in FIG. 1, the stocking 10 is held stationary by the stocking support (i.e. pin bar 11) and the geometric body 16 is pulled along the length of the stocking by rod 17, which is in turn operatively connected to a drive mechanism 18 having a load sensor 19 and device 20 for measuring and recording the force required to pull the geometric body through the stocking. Preferably, the device continuously records the force, such that variations in donning forces experienced by a wearer can be observed throughout the donning process.

Figure 4:
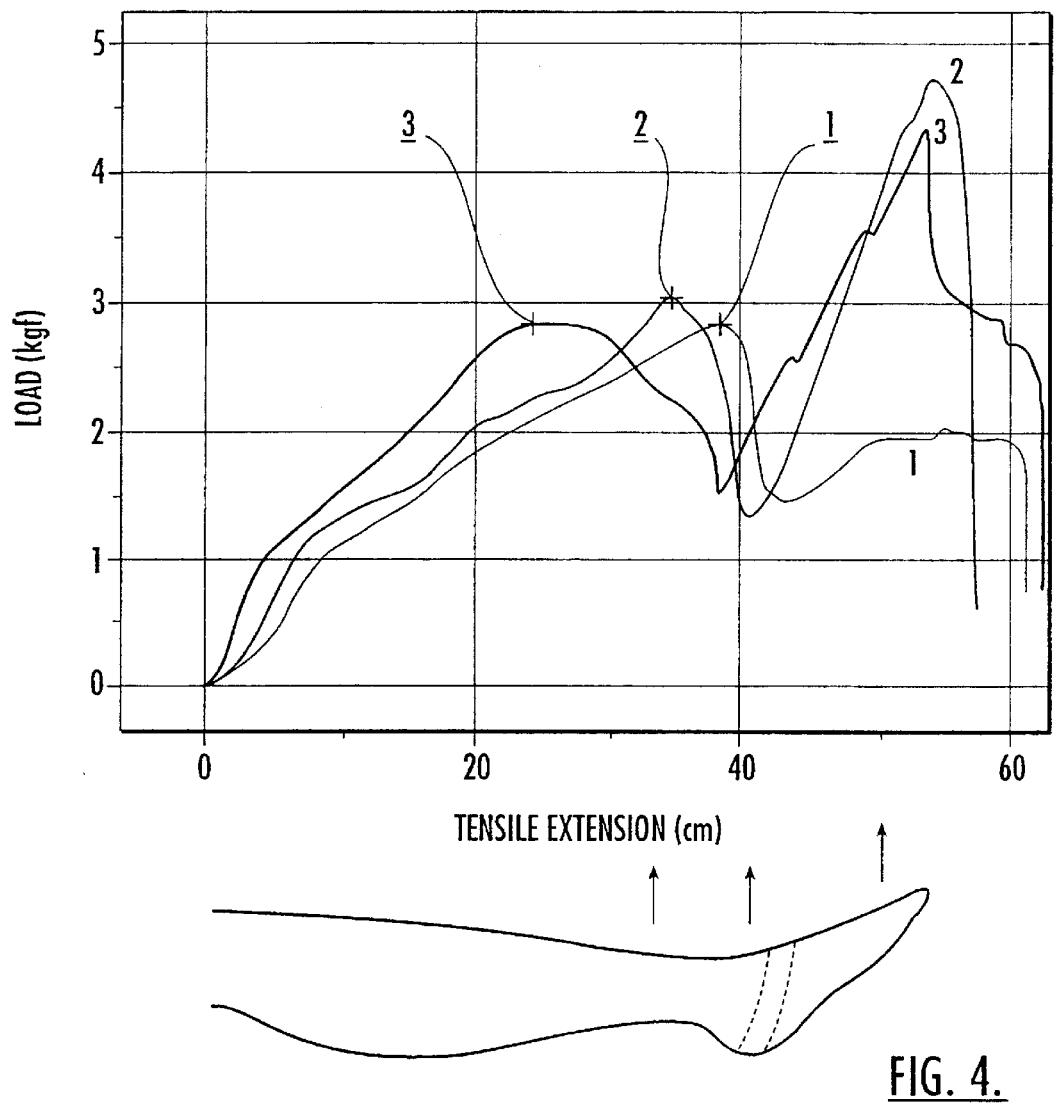
FIG. 4 illustrates the influence of design of three different stockings each with a similar degree of compression, each manufactured by a different manufacturer with an outline of a leg beneath it to illustrate the changes and the curve of the graph experienced as the tester head passes through different portions of the stockings.

FIGS. 3 and 4 each illustrate graphical representations recorded using the above-described test method to compare various stocking samples. In FIG. 3, two stockings having different degrees of compression (30–40 mmHg and 20–30 mmHg), which were manufactured by the same manufacturer, were tested according to the method described above. The results illustrated the influence of the compression forces which experienced throughout the process of donning each of these stockings. The curves of the graph show the tension experienced as the geometric body passes through different portions of the stocking (namely, the ankle, heel and foot). As can be seen from the graph, the highest point on each of the curves is experienced when the geometric body passes through the ankle portion of the stocking, as this is generally the region of highest compression and smallest circumference. The stockings can be marked in any conventional manner so that the specific regions of the stocking can readily be determined. For example, the stocking can be marked with a pen by hand, different colored yarns can be employed during the knitting process to indicate the different regions, or the like.

FIG. 4 shows a similar type of graph, which illustrates the influence of design of three different stockings (each manufactured by a different manufacturer) which were tested according to the method described above with respect to FIG. 1. By utilizing this test method, a comparison can readily be made between the donning properties of one competitor's products with those of another, and between various different products of a single manufacturer. Therefore, it enables a method for substantiating claims by a manufacturer that its products are easier to don than those of another, as well as providing valuable information as to the impact of various modifications to a product (e.g. finishes, knit structure, yarns used, etc.) on donnability of the final product.

By utilizing this comparative data, the determinations with respect to the design of the stockings can be readily made. For example, it may be determined that the friction between the stocking and the wearer is too great, and particular finishes should be employed in order to reduce the friction. Likewise, it may be determined that the donning forces are too great in a particular portion of the stocking. As a result, this method enables the measurement of the donning process and therefore enables comparison of the forces needed to don one stocking with those needed to don another. Therefore, objective determinations can be made with respect to which of a number of stockings would be easier to apply by a wearer, as opposed to prior tests which simply relied on the subjective impression of the person donning the stockings.

Although for purposes of illustration, the invention has been described in connection with stockings, it is to be noted that other types of tubular articles may also benefit from testing by the instant method, including but not limited to T-shirts, arm supports, and the like. In other words, the method is intended for use in any application where it would be desirable to obtain data relating to the resistance a tubular article has to another item being inserted into it.

By virtue of this new method, valuable information can be obtained which can be used in the design and comparison of products, such as the effects on donnability of various softeners and finishes, fiber selection, knit structure selection, type of yarns to be used, types of fibers to be used, etc. As a result, manufacturers can obtain concrete data with respect to whether a particular product is easier to don than another, and the effects of modifications to a product on the donning curve can be readily evaluated.

In addition, the method can be performed by the continuous pulling or pushing of the geometric body through the stocking or the pulling or pushing of the stocking over the geometric body, or the motion can be in a start-stop-start intermittent motion, more closely approximating that actually encountered during the donning process of a stocking.

As noted above, the relative movement between the geometric body and the stocking can be performed in any of a variety of ways. For example, the embodiment shown in FIG. 1 illustrates the stocking 10 being held in a fixed position while the geometric body 16 is pulled through it. Furthermore, the stocking could be held in a fixed position and the geometric body pushed rather than pulled through it, or the geometric body could be held in a fixed position and the stocking pushed over it; in other words, the invention encompasses all methods for causing relative movement between such a geometric body and a stocking.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for testing the forces experienced by a wearer when donning a tubular article comprising the steps of:
   securing an end of said tubular article adapted to be worn by a human to a support;
   inserting a tension testing head having a geometric body within said tubular article;
   passing said tension testing head having a geometric body through said interior of said tubular article; and
   measuring the force used to advance said geometric body and extension of said tubular article.

2. The method according to claim 1 wherein the step of advancing comprises pushing said geometric body through said tubular article.

3. The method according to claim 1 wherein the step of advancing comprises pulling said geometric body through said tubular article.

4. The method according to claim 1 wherein the step of advancing comprises pulling said tubular article over said geometric body.

5. The method according to claim 1 further comprising recording the force used to advance said geometric body and extension of said tubular article.

6. A device for testing the forces experienced by a wearer when donning a tubular article comprising:
   support means for securing one end of said tubular article adapted to be worn;
   a geometric body attached to a rod adapted to be pulled or pushed through said tubular article;
   means for moving said geometric body through said tubular article; and means for measuring the tension within said tubular article.

7. A device for testing the forces experienced by a wearer when donning a tubular article comprising:
   support means for securing one end of said tubular article adapted to be worn;
   a geometric body attached to a rod adapted to be pulled or pushed through said tubular article;
   means for moving said geometric body through said tubular article;
   means for measuring the tension within said tubular article; and
   wherein said securing comprises retaining the end of said tubular article to a pin bar assembly.

8. The method according to claim 1 wherein said geometric body is shaped to simulate a portion of a human foot.

9. The device according to claim 6 wherein said geometric body has a torus shape.

10. The device according to claim 6 further comprising tension recording means.

11. The method according to claim 1 wherein said tubular article adapted to be worn by a human is a hosiery article.

* * * * *